United States Patent [19]

Buffet et al.

[11] Patent Number: 4,921,487
[45] Date of Patent: May 1, 1990

[54] EXTERNAL DEVICE FOR INJECTING MEDICINE

[75] Inventors: Jacques Buffet, Villemomble; Jean-Paul Buffet, Le Raincy; Jean Piani; Francois Paravisini, both of Ajaccio, all of France

[73] Assignee: Compagnie Financiere Saint. Nicolas, Le Raincy, France

[21] Appl. No.: 247,271

[22] Filed: Sep. 21, 1988

[51] Int. Cl.⁵ .............................................. A61M 5/20
[52] U.S. Cl. .................................. 609/135; 604/154; 604/208; 128/DIG. 12
[58] Field of Search ............... 604/208, 218, 154, 155, 604/151, 135, 224; 128/DIG. 12, DIG. 13; 222/333, 390

[56] References Cited

U.S. PATENT DOCUMENTS

| 3,384,080 | 5/1968 | Muller . |
| 3,709,636 | 1/1973 | Rosenberg . |
| 4,059,110 | 11/1987 | Wuthrich et al. ............... 604/135 |
| 4,300,554 | 11/1981 | Hessberg et al. ............... 604/135 |
| 4,634,431 | 6/1987 | Whitney et al. ............... 604/154 |
| 4,652,260 | 3/1987 | Fenton, Jr. et al. ............... 604/154 |
| 4,662,872 | 5/1987 | Cané ............... 604/154 X |
| 4,676,122 | 6/1987 | Szabo et al. ............... 604/154 X |

FOREIGN PATENT DOCUMENTS

WO82/00589 3/1982 PCT Int'l Appl. .
WO85/01443 4/1985 PCT Int'l Appl. .
2109690 2/1981 United Kingdom .

Primary Examiner—Stephen C. Pellegrino
Attorney, Agent, or Firm—Mason, Fenwick & Lawrence

[57] ABSTRACT

A casing holds a syringe that contains a medicine, such as insulin, which may be driven out of the syringe by a plunger into a catheter attached to a human body. The power for the plunger drive mechanism is provided by a spiral spring mounted in the casing. A clockwork movement, regulated by a step electrical motor, controls the speed of the drive mechanism. A microprocessor controls the speed of the step electrical motor which regulates the clockwork movement. All of the components are contained in a casing which has an opening to allow the position of the plunger in the syringe to be seen from outside the casing.

6 Claims, 8 Drawing Sheets

EXTERNAL DEVICE FOR INJECTING MEDICINE

External Device for Injecting a Medicament

The invention concerns an external device for injecting a medicament.

More particularly, it concerns a device for the injection of insulin in particular into the human body of the type comprising an inlet, an outlet, and mobile transfer means interposed between the inlet and the outlet comprising a mobile drive member, first mobile drive means, connected to the mobile member and ensuring its displacement, and a mechanical power supply connected to the first drive means and designed to supply the necessary power to drive them.

Numerous devices of this type are known, each having disadvantages which the invention simultaneously resolves.

The French patents FR 2 282 912, FR 2 495 942, FR 2 348 709, the German patent DE 600 202, and the U.S. Pat. No. 3,709,636 describe complex, bulky injection systems actuated by electric motors which consume a lot of energy.

The patent applications PCT WO 85 01443 and WO 82 00589, like the U.S. Pat. No. 3,384,080, describe mechanically actuated systems with which it is not possible, however, to inject instant doses.

The British patent application GB 2 109 690 describes a syringe particularly designed for insulin injection. It is actuated manually.

The object of the invention, then, is to propose an external device for injecting a medicament which has the advantages of a mechanical power supply, has a reliable regulating means and with which it is possible to inject instant doses.

To this end, the invention concerns a device of the type mentioned above which comprises regulating means connected to the first drive means and designed in such a way that the first drive means and the means for the simultaneous administration of instant doses or boluses may be regulated.

According to a first embodiment the mobile member of the drive mechanism is the plunger of a syringe, the regulation means are mechanical, and the device is portable.

According to a second embodiment, the regulating means of the device according to claim 1, characterised in that the regulating means are at least partly electrical or electronic.

The other characteristics of the invention will emerge from the following description with reference to the attached drawings in which.

Figure 1:
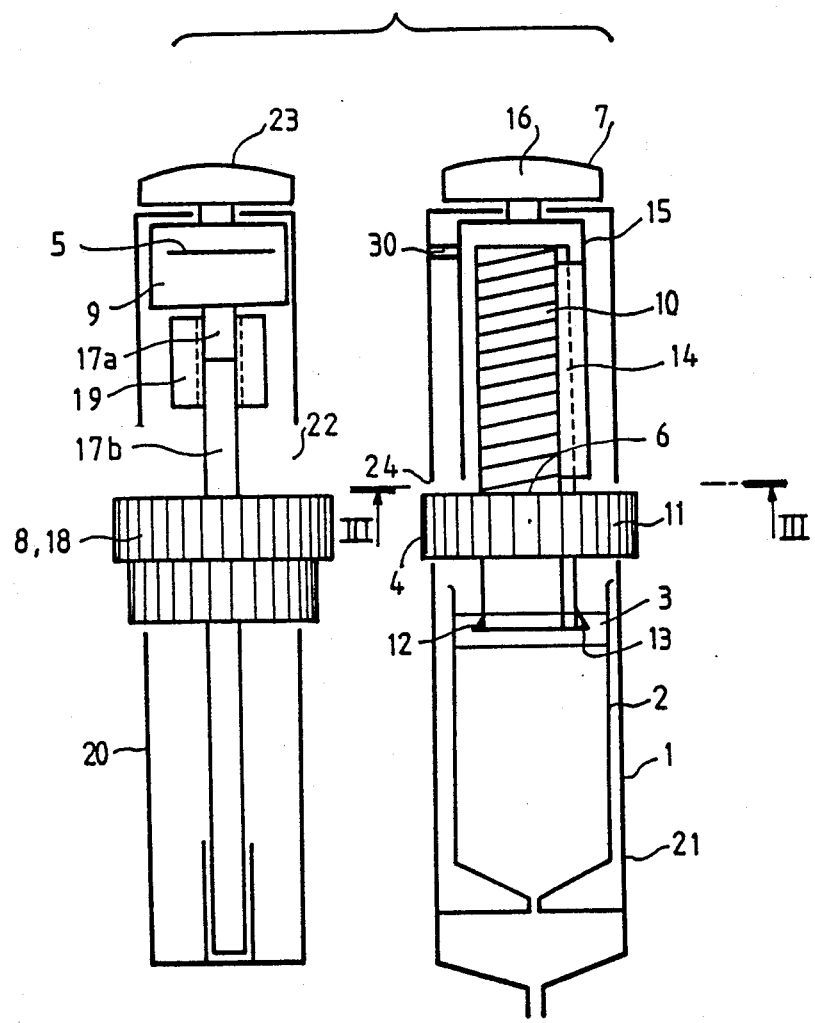
FIG. 1 is a section diagram in the axial plane illustrating the device according to the first embodiment of the invention, the two parts of the device being separated for the sake of clarity.
Figure 2:
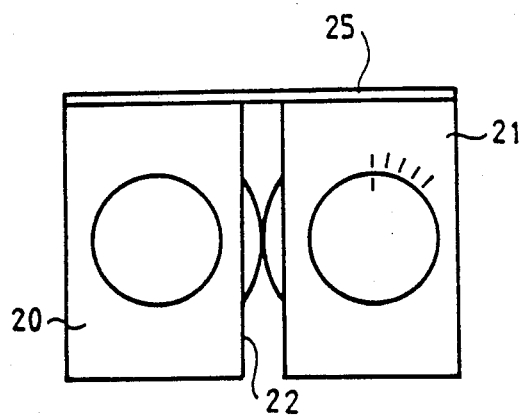
FIG. 2 is a plan diagram of the device according to the invention in order to show how the two parts of the case cooperate.
Figure 3:
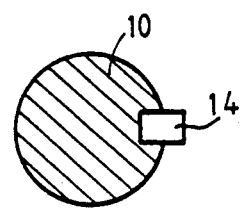
FIG. 3 is a view of FIG. 1 in transverse section along the line III—III.
Figure 4:
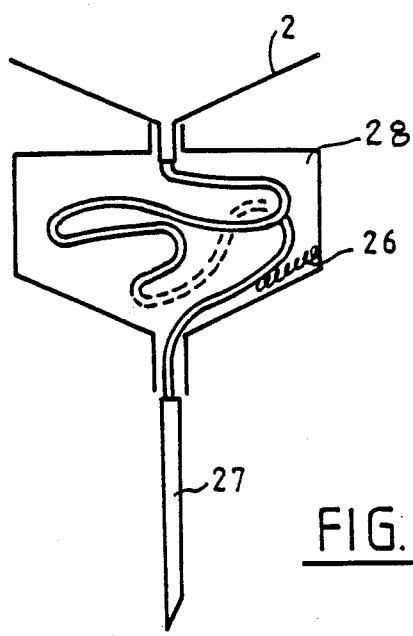
FIG. 4 is an enlarged view of the reservoir and the means of retracting the catheter.
Figure 5:
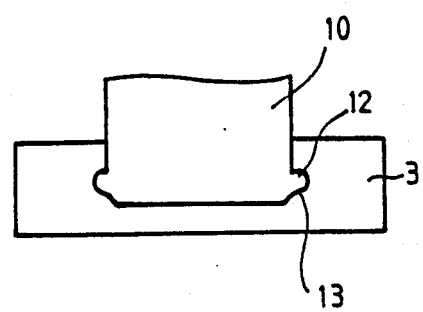
FIG. 5 is an enlarged view of the means of connecting the endless screw and the plunger.

First of all, a first embodiment of the invention will be described with reference to FIGS. 1 to 7.

The invention concerns an external device for injecting a medicament for example, in particular insulin, into the human body, of the type comprising a portable casing 1 (represented only partially and diagramatically), a syringe 2 having a detachable plunger 3 mounted in the casing 1, means 4 of driving the plunger 3 by axial sliding comprising means 5 of energy storage and automatic linear drive means 6 of the plunger 3 actuated by the power stored in the energy storage means 5, as well as manual means 7 of linear drive with an actuating wheel 16.

With the device according to the invention, instant doses or boluses may be administered simultaneously by virtue of the manual means 7, as will be seen below, and furthermore, continuous doses may be administered at a constant rate or at a basic rate by virtue of the energy storage means 5 and the automatic drive means 6.

According to the invention, the means 5 of storing energy are mechanical, integral with the casing 1 and are comprised in particular of elastic means. The automatic drive means are also mechanical. The automatic drive means are comprised of means 9 of regulating the movement generated by the means 5 of storing energy, in particular by the slackening of the elastic means 5, and the mechanical means 8 of transmitting movement to the plunger 3.

The energy storage means 5 only serve to set the automatic motor means 6 of linear drive in motion to administer the basic flow, whereas, as stated above, the administration of the bolus is carried out only by the actuation of manual means 7 of linear drive.

Preferably, the means 5 of storing energy consist of a spring, in particular a spiral spring, while the regulating means 9 comprise a mechanical clockwork movement 9 with an escapement and horizontal lever driven by the spiral spring.

The linear drive means 4 also comprise an endless screw 10 which cooperates with a nut 11. The nut 11 is rotatable, is blocked axially by the casing 1 in particular, and forms a driven pinion on the outside. The endless screw 10 is principally non-rotatable, notwithstanding what is said below, and axially mobile with respect to a sheath 15 mounted pivotably in the casing 1. The endless screw 10 ends on the side of the syringe 2 with a peripheral projection 12 which cooperates in a detachable fashion with force in a peripheral groove 13 of the plunger 3. The projection 12 and the groove 13 form means 12, 13 of rigid, detachable connexion between the screw 10 and the plunger 3.

The endless screw 10 is non-rotational with respect to the sheath 15 by virtue of at least 1 key 14 extending axially. The key 14 is carried by the sheath 15 mounted pivotably in the casing to which the wheel for manual actuation is secured.

The sheath 15 is made non-rotatable with respect to the casing 1, preferably in only one rotational direction, by locking means 30 with a reverse-lock catch. It is thus locked in one direction and free in the other direction. Preferably, the means 8 of transmission comprise detachable, replaceable speed regulating members.

The means 8 of transmission further comprise an axle 17 on to which is splined at least one motor pinion 18 which cooperates with the nut forming the driven pinion 11. The axle 17 is driven in rotation by the mechanical clockwork movement 9.

Preferably, torque-limiting means 19 are interposed between the motor pinion 18 and the clockwork movement 9 on the axle 17 and in two parts 17a, 17b. With the torque-limiting means 19 it is possible to avoid deterioration of the catheter 27, in particular when the latter is closed, by applying too great a pressure.

The detachable replaceable speed regulating members of the transmission means 8 are formed, for example, by a plurality of motor pinions 18 of different diameters, each of which is capable of cooperating with the driven pinion 11 and is connected rigidly, but detachably, to the axle 17 or to a part 17a of the said axle. For example, the motor pinions 18 comprise an axial bore equipped with radial toothing (ie for which the teeth have their radial height) capable of cooperating with radial toothing extending along the axle 17 and integral with the latter or the part 17a.

The casing 1 comprises preferably two parts 20, 21, the first part 20 in which the axle 17 is mounted, the pinion or pinions 18, the torque-limiting means 19 and the clockwork movement 9. The first part 20 comprises a lateral window 22 for access to the teeth of the pinion or pinions 18 from which a part of the periphery of the pinion or pinions 18 projects in order that they may cooperate with the other pinion 11. Finally, a winder 23 is placed on the outside of the first part 20 for winding up the spring 5 of the clockwork movement 9.

The second part 21 comprises on one side a groove in which the syringe 2 is mounted and on the other side the sheath 15 with its key 14, the endless screw 10 cooperating with the nut 11 forming a driven pinion. The nut 11 forming the driven pinion projects from a window 24 of the second part 21 in order to cooperate with the pinion or pinions 18.

With detachable connecting means 25 represented diagrammatically only, it is possible to connect the two parts 20 and 21 together in a rigid, but detachable, manner so that the pinions 11, 18 cooperate with one another.

According to another characteristic, a groove 28 is provided at the end of the second part 21, forming a reservoir for the catheter and means 26 for retracting the catheter 27 connected to the syringe 2 in the said groove. The retraction means 26 may consist of one or more springs. As a variation, they consist of a large-pitch wheel of an internal screw mounted at the outlet of the groove 28 which permits the removal of the catheter 27 from the groove 28, but which forces the catheter in the opposite direction into the groove when it is turned. The means retraction means 26 may also consist of a retracting spiral spring of a reel around which the catheter 7 is wound. By means of the groove 28 and the retraction means 26 it is possible to avoid too long a portion of the catheter 27 remaining outside, but at the same time providing the required length of catheter 27.

Figure 6:
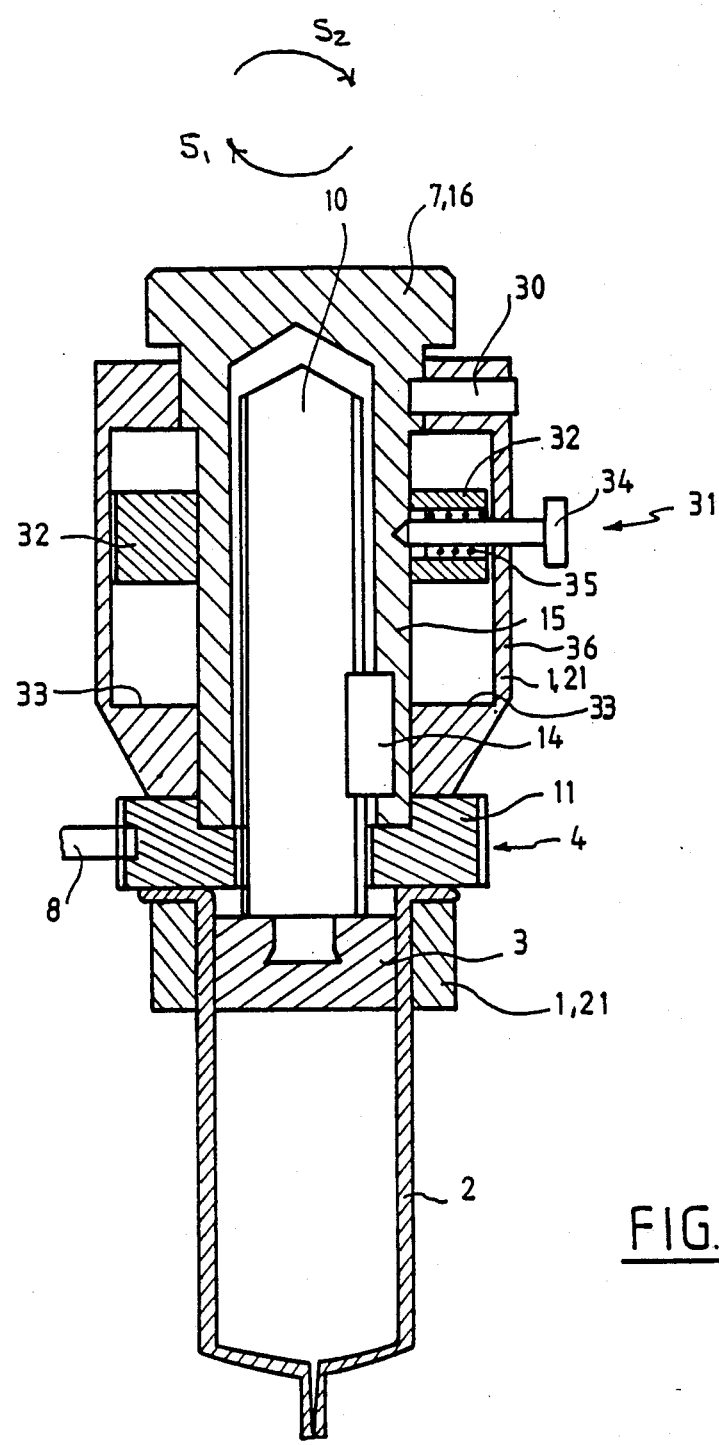
FIG. 6 is a section diagram in the axial plane showing the second part of another embodiment of the invention.

FIG. 6 shows another embodiment of the part 21 of the device according to the invention carrying the syringe.

The means 30 of locking the sheath 15 with respect to the casing comprise at least one spring reverse-lock catch 30 which cooperates with radially external peripheral teeth on the sheath 15 to make the latter non-rotatable in the rotational direction S1. On the other hand, these locking means 30 leave the sheath 15 free to turn in the other direction S2 when the wheel 16 is actuated manually. In this case the noises caused by the reverse-lock catch 30 as each tooth of the sheath 15 passes over it enable the user to control the degree of rotation imposed on the wheel 16. Gradations may be provided in the vicinity of the teeth on the sheath 15 or on the wheel 16 for the purpose of visual control of rotation by the user. The locking means 30 therefore also serve as precision feed means for the manually injected dose.

Furthermore, the device as shown in FIG. 6 comprises means 31 of limiting the injected manual dose, comprising a ring 32 exterior to the sheath 15 and cooperating with an exterior coarse-pitch thread of the sheath 15, in such a way that the rotation of the sheath 15 in the direction S2 causes the ring 32 to slide towards a limit stop 33 of the casing 1, simultaneously and proportionally to the axial displacement of the screw 10. By means of a pin 34, the point of which is retracted by a spring 35 in the outer thread of the sheath 15, it is possible to position the ring at the height corresponding to the required dose. The pin 34 passes through and slides into a slot 36 in the casing 1 which advantageously comprises graduations or marks. To inject a dose manually, the user therefore positions the ring 32 by pulling the pin 34 out of the thread of the sheath 15 and then making the ring 32 slide in such a manner as to place the pin 34 opposite the mark on the casing corresponding to the required dose or the maximum dose. The user then releases the pin 34 which once more cooperates with the thread of the sheath 15, then turns the wheel 16 in the direction S2. The rotation is stopped when the ring 32 reaches the limit stop 33, thus preventing the injection of too heavy a manual dose.

During the manual rotation of the wheel 16, the nut 11 is locked by the automatic drive means 7, in particular by the regulating means 9, the clockwork movement of which is impeded.

When the motor pinion 18 cooperates with the pinion 11 to drive the plunger 3 automatically the sheath 15 is inclined to turn in the direction S1 with respect to the casing and is thus locked by the locking means 30. Thus the screw 10 is also made non-rotatable and moves axially.

Figure 7:
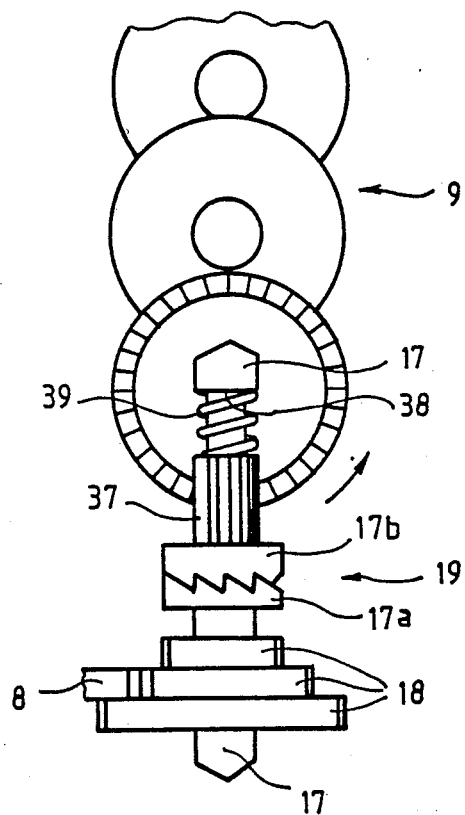
FIG. 7 is a diagram illustrating an embodiment of the torque limiting means according to the invention.
Figure 8:
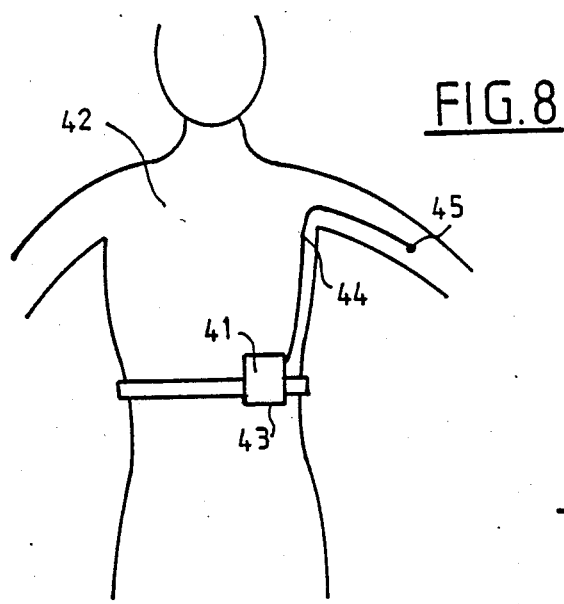
FIG. 8 is a diagram illustrating the general use, which is known per se, of an injection pump for medicaments.
Figure 9:
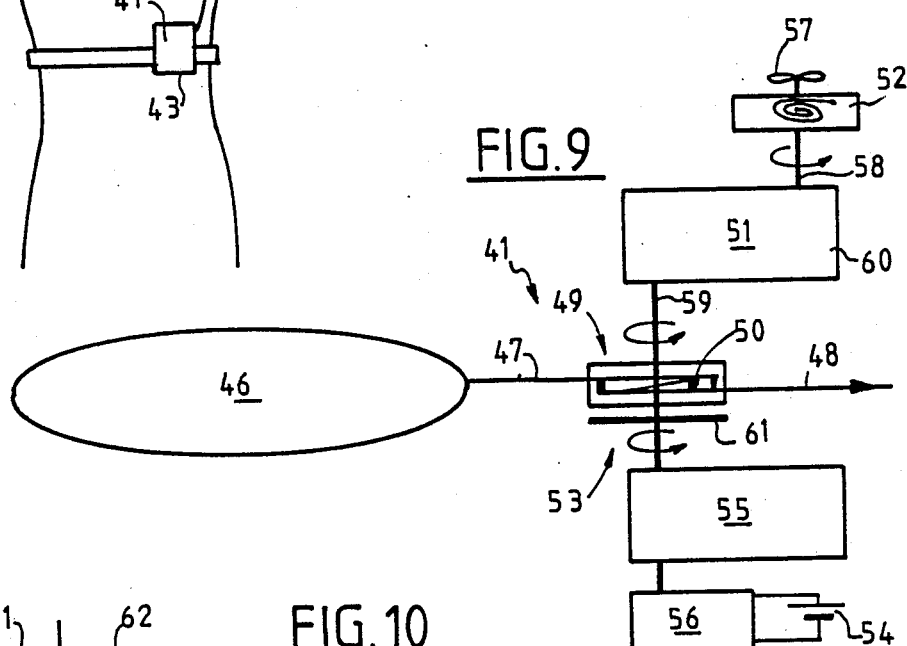
FIG. 9 shows a view in elevation of the device according to the second embodiment of the invention.
Figure 10:
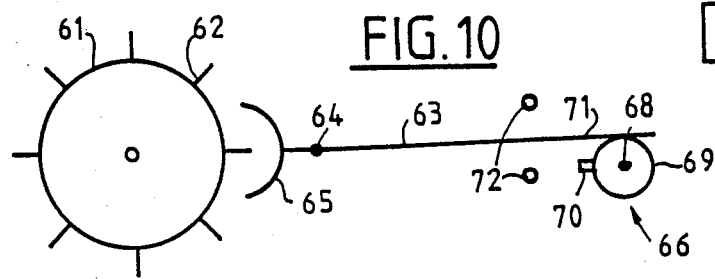
FIG. 10 shows a view in elevation of the regulating means of the device according to the second embodiment of the invention.
Figure 11:
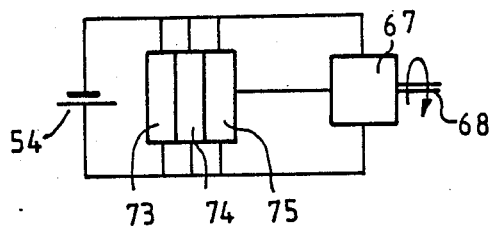
FIG. 11 shows a view in elevation of the regulating means of the device according to the second embodiment of the invention.

The torque-limiting means 19 shown in FIG. 7 are formed by a first toothed rim 17a which is integral with the axle 17 and the motor pinions 18, and a second toothed rim 17b which cooperates with the first toothed rim 17a. The teeth of the rims 17a, 17b are axial, i.e. extend vertically almost in parallel with the axle 17 and slant in order to allow the rims 17a and 17b to slide in the case of axial deplacement of the rims with respect to one another if the rim 17a which is integral with the motor pinions 18 were to become locked. The second rim 17b carries a pinion 37 driven by the clockwork movement 19. The rim 17b and the pinion 37 are penetrated by the axle 17 on the end of which is a limit stop 38 at its end cooperating with a compression spring 39 which, in turn, cooperates with the pinion 37 or the rim 17b to retract the rim 17b against the first rim 17a with a given force.

When the torque transmitted by the two rims 17a, 17b exceeds a certain value, the axial reaction of the teeth of the rims becomes equal or superior to the retracting force of the spring 39, which causes the axial displacement of the rim 17b and the sliding of the rims 17a, 17b with respect to one another. Means of alerting the user in the case of sliding of the rims 17a, 17b with respect to one another are advantageously provided. For example, the axial displacement of the rim 17b leads to the release of the spring 5 of the storage means, and a contacter causes a ringing when the spring is completely released.

Now a second embodiment of the invention will be described with reference to FIGS. 8 to 12.

The invention concerns a device 41 designed to be carried by a patient 42 and to this end carried in a holster 43 and to which a catheter 44 is connected, the end 45 of which is introduced into one of the patient's 42 veins.

The device 41 is, for example, designed for the injection of insulin, cancer drugs, hormones or any other appropriate product.

The device 41 may be in particular of the peristaltic kind, which is known per se and does not directly constitute the subject of the invention.

The device 41 is naturally connected to a storage facility of the medicament 46. This facility 46 consists, for example, of a fluid pocket.

The injection pump 41 comprises, in a manner known per se, an inlet 47 and an outlet 48 designed to be connected respectively to the facility 46 and the catheter 44, and of mobile transfer means 49 interposed between the inlet and the outlet 47, 48. The mobile transfer means 49 comprise: a mobile drive member for the medicament 50, first drive means 51, which are mobile, are connected to the member 50 and effect its movement, and finally a power supply 52 connected to the first drive means 51 and capable of supplying the first drive means 51 with the power necessary for them to function and be driven.

If the device 41 comprises a peristaltic pump, the mobile member 50 is formed by the mobile peripheral rollers of a wheel placed in a housing in such a manner that a flexible tube connecting the inlet 47 and the outlet 48, i.e. the facility 46 and the catheter 44, may be placed between the housing and the rollers so that it can be squeezed by the rollers defining a known volume of medicament in motion.

According to the invention, the power supply 52 is mechanical and the device 41 comprises electrical or electronic regulating means 53 connected to the first drive means 51 and making it possible to control the action of the first drive means 51.

The regulating means 53 comprise firstly an electric power supply 54, secondly second mobile drive means 55, to which the electric power supply 54 is connected and which cooperate with the first drive means 51, and thirdly, electric or electronic means of controlling 56 the second drive means 55.

As will be seen below, the second drive means 55 are of the type with an intermittent all-or-nothing action according to a cycle of action defined by the control means 56. The second drive means 55 cooperate functionally with the first drive means 51 in such a manner that during the periods when the second drive means 55 are at rest, the first drive means 51 are also kept at rest, and that in the opposite case, during the period when the second drive means 55 are in motion, the first drive means 51 are also in motion by virtue of the mechanical power supply connected to them. As stated above, the succession of periods of rest and motion of the second drive means 55 is determined by the control means 56.

The mechanical power supply 52 consists for example of a spring, in particular a spiral spring, which may be tensioned by means of a winding mechanism 57. The first drive means 51 are also of a mechanical type and comprise in particular an input axle 58 connected to the spring 52 and an output axle 59 connected to the mobile drive member for the medicaments 50. Taking into account the structure of the device 41 and the usual quantitive characteristics for this kind of pump, obviously the mechanical power supply 52 must be sufficiently powerful to drive the mobile member 50.

If need be, and in a manner known per se, a series of reducing gears 60 is interposed between the input axle 58 and the output axle 59.

In a preferred embodiment, the second drive means 55 are splined on to the output axle 59 of the first drive means on which, in the case of a peristaltic-type pump, the roller wheel previously mentioned is also splined.

The second drive means 55 may form the subject of numerous embodiments according to the requirements. In particular, the second drive means 55 are of the mechanical type and may comprise a toothed wheel 61 splined on to the output axle 59 and having peripheral teeth 62 regularly spaced around the axle; a lever 63 pivotably mounted about an axle 64, comprising at one end an anchor 65 which cooperates with the teeth 62. By virtue of the means 66 it is possible to make the lever 63 pivot about its axle 64 in such a manner that, by virtue of the cooperation of the anchor 65 and the teeth 62 of the toothed wheel 61, the latter carries out successive pivotings of the degree of the angle separating the two successive teeth at each alternate reciprocating movement of the lever 63.

The means 66 to make the lever 63 pivot may comprise an electric motor 67 of the step-by-step type, a wheel 69 being splined on to the output axle 38 thereof and comprising at least one tappet, projection or such like 70 cooperating with the free end portion 71 of the lever 63 opposite the anchor 65.

Preferably, furthermore, limit stops 72 limiting the pivot range of the lever 63 and a spring or such like acting on the lever 63 on the wheel 69 may be provided.

The electric power supply 54 may consist of a continuous current cell, in particular a 3-volt lithium cell. As emerges from the preceding description and the explanations which follow, the electric power supplied by the electric power supply 54 is weak since it is only intended to operate the regulating means 53, in particular the movement of the lever 63. Consequently, the electric power supply 54 can be limited in strength and long-lasting, in particular non-replaceable.

The control means 56 of the second drive means 55 may comprise, for example, an oscillator 73 with adjustable frequency and a counting circuit 74 capable of producing series of impulses at predetermined intervals and, to this end, being adjustable by means of potentiometers or decade contactors 75.

By virtue of an operation of the potentiometers or decade contactors 75, it is possible to control the series of impulses controlling the operation of the motor 67, and hence of the lever 63, and consequently, the rotation of the toothed wheel 61. When the toothed wheel 61 is freed on the pivoting of the lever 63, it is driven by the first drive means 51.

The contactors comprise means by which, without altering a previously fixed flow adjustment, it is possible to keep the motor 67 operating continuously for as long as the contactors are actuated, thus permitting the admistration of instant doses.

According to another embodiment, the administration of instant doses is obtained by direct manual action on the mobile drive member.

Figure 12:
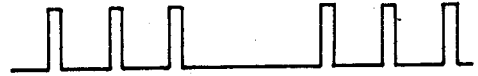
FIG. 12 shows a front view of the preferred embodiment of the invention.
Figure 13:
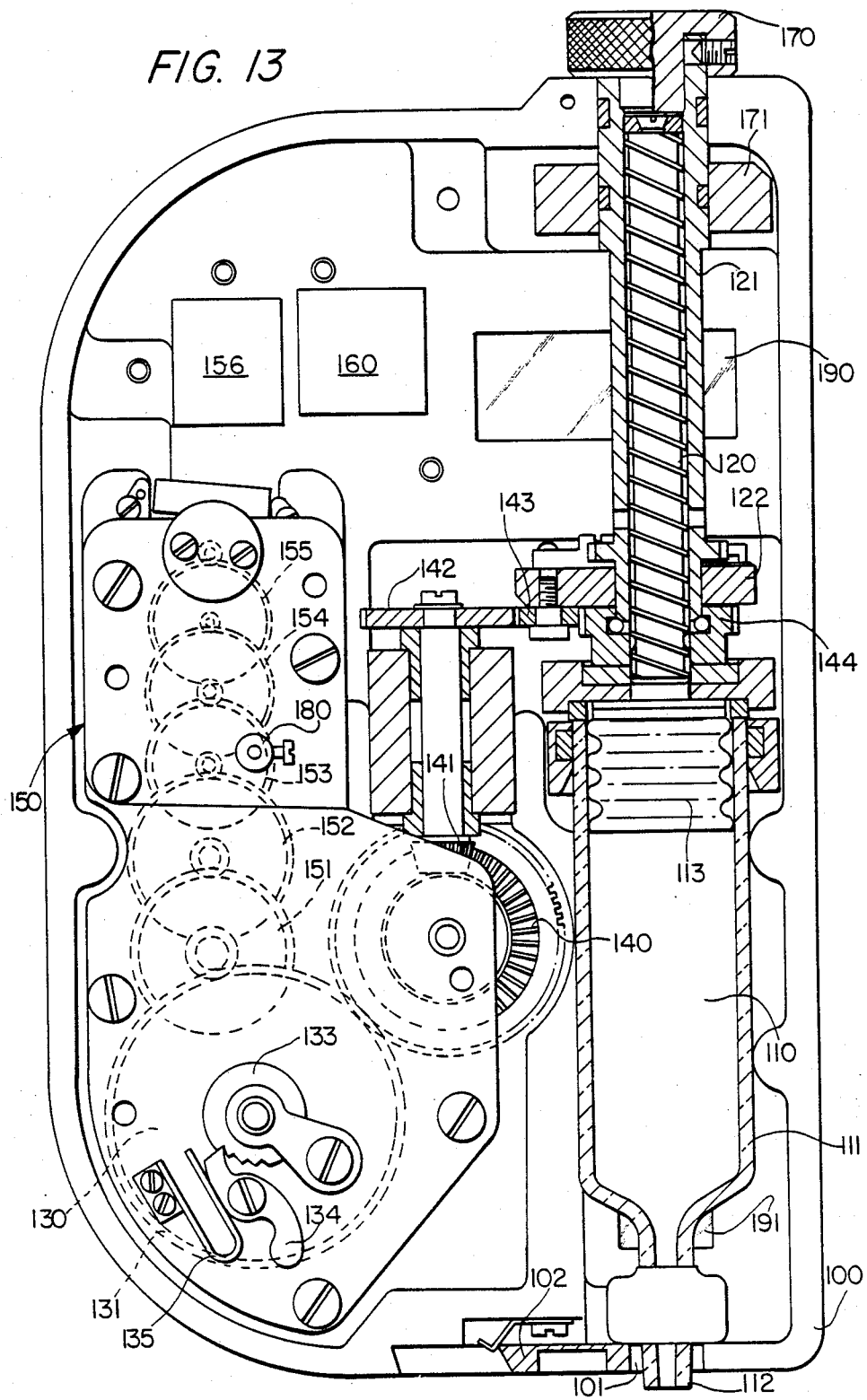
FIG. 13 shows a side view of the preferred embodiment of the invention.
Figure 14:
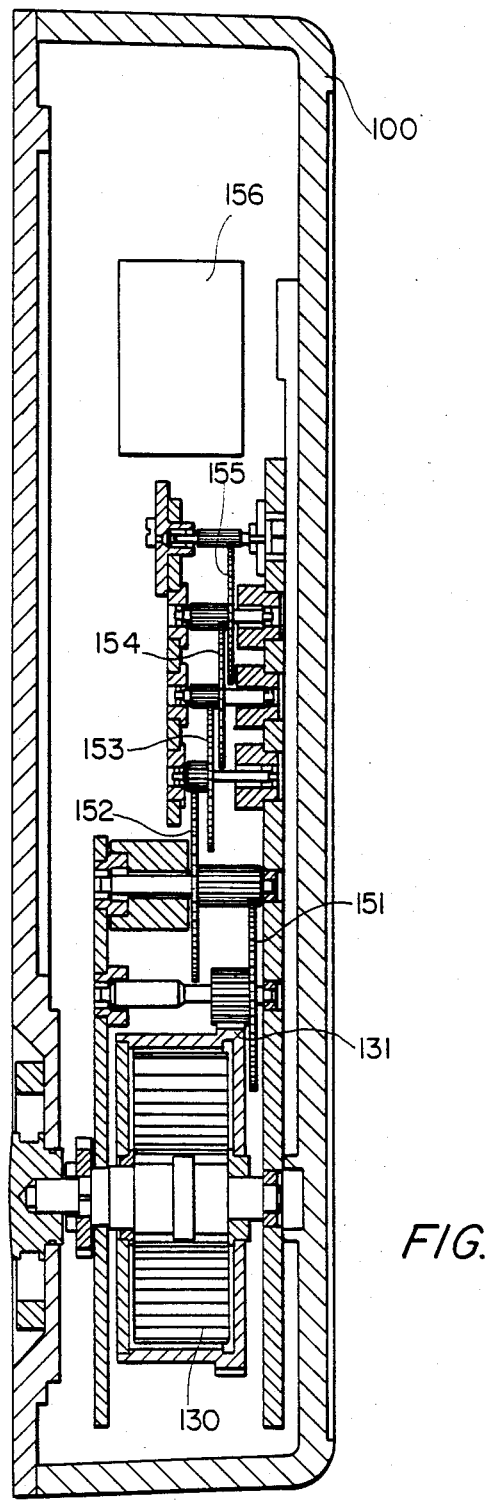
FIG. 14 shows an outside front of view of the preferred embodiment of the invention.
Figure 15:
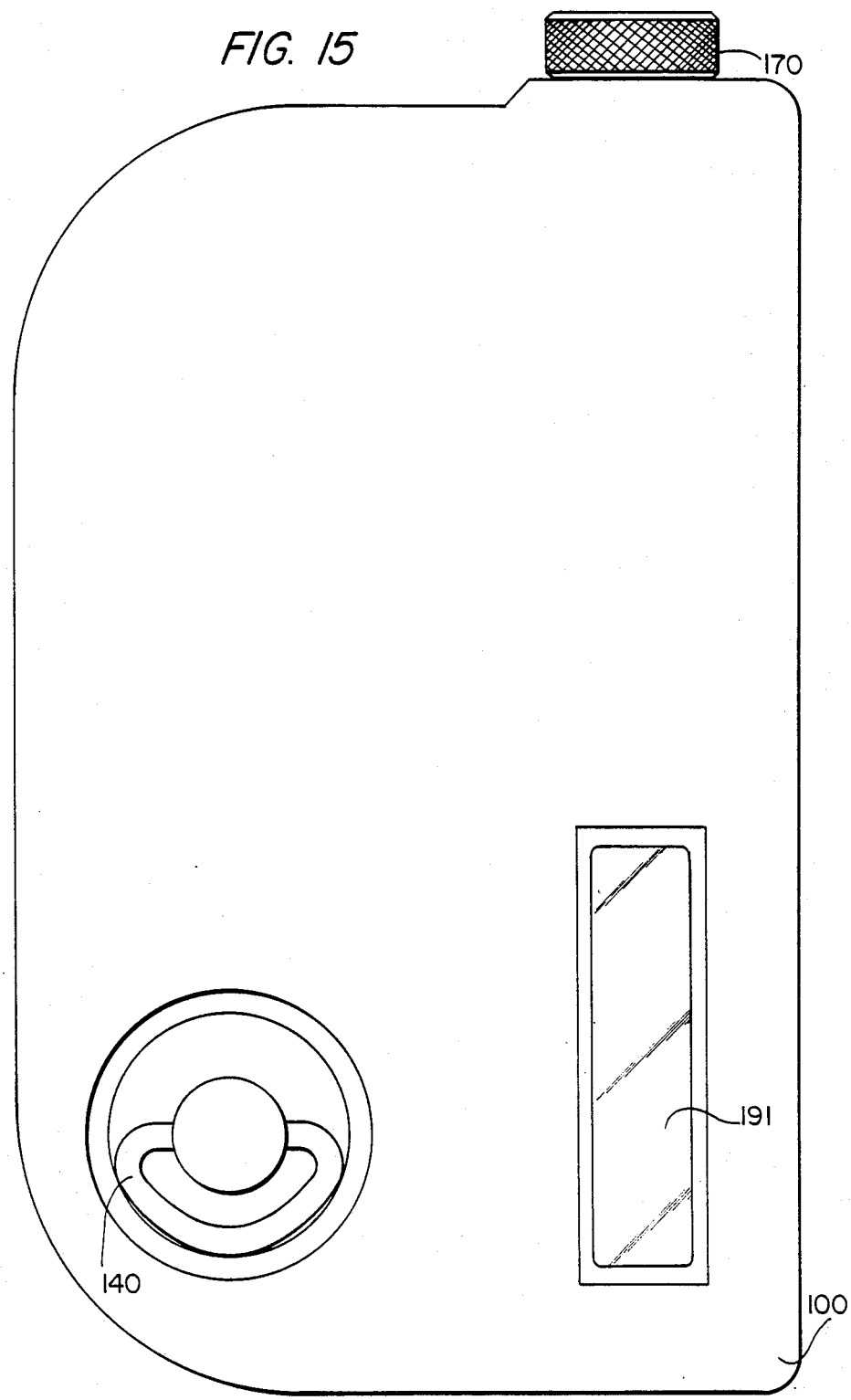

The preferred embodiment of the invention will now be described with reference to FIGS. 12, 13 and 14.

The external device for injecting a medicament according to the invention comprises a casing 100 which can receive a syringe 110. This one can be introduced through the aperture 101 when the slide 102 is slided off and it is maintained in due position when the slide is slide on as represented on the figure.

The syringe comprises a housing 11 which ended on one side by a neck 112 which can be linked to a catheter permitting the injection in a human body. It comprises also a piston 113 which has to be moved forward to inject the medicament.

The movement of the piston is produced by the displacement of the sheath 120 which is externally grooved. This sheath 120 is guided by the tube 121 fixed to the casing 100 and works with the nut 122 also fixed to the casing 100 so that it moves longitudinally when it is rotated.

Its rotation can be produced either automatically by actuating means or by a manual action.

The self-acting rotation is slow and regular. The energy needed in this case comes from a spiral spring 130 one end of which is fixed to a main ratchet wheel 131 and the other to the casing 100. It can be manualy stretched from outside the casing by use of a handle 132 and is maintained stretched by the cooperation of a ratchet wheel 133 with a ratchet 134 is moved back to its work position by a spring 135.

The energy of the spiral spring 130 is transmitted to the sheath 120 by the gear wheel 140, the conical gear 141 and the gear wheels 142, 143, 144. The late wheel 144 being fixed to the sheath 120.

The speed of the main ratchet wheel 131 when transmitting energy to the sheath 120 is regulated by the clockwork movement 150. This one comprises reduction gears 151, 152, 153, 154, 155 cooperating with the said main ratchet wheel, the movement of the last wheel being regulated by a step by step electrical motor 156. This one is only symbolically represented on the FIGS. 12 and 13. Its connection with the wheel 155 is of the type represented on FIG. 10 and explained above.

This motor is monitored by an electronic device 160 comprising a microprocessor. This microprocessor permits to choose the speed of the motor for different periods of the day.

It is pointed out that the clockwork movement 150 is distinct from the gears transmitting the power to the sheath. This makes the device reliable and prevent its destruction even if it is made working without any syringe in it.

The manual action is produced by the rotation of the handle 170 located outside the casing with drive the sheath 120 by the nut 171. The manual action permits the injection of instantaneous doses in addition to the regulated injection.

In order to prevent the sheath 120 to turn backward, this one is provided with a ratchet wheel 123 usualy cooperating with the ratchet 124. When the nut 171 turned in the direction that forwards the piston it will drive the sheath 120, when turned in the other direction it will have no effect.

When changing the syringe, the ratchet 124 is released from the ratchet wheel 123 in order to allow backward movement of the sheath 120.

A sensing device 180 connected to the microprocessor checks the proper working of the mechanical part of the device and produces a sound alarm when anything is wrong. The sensing device comprises wire regularly moved by one of the reduction gear of the clockwork when it is running.

This casing 100 comprises a first window 103 allowing the user to check the level of the piston 113 in the syringe and a second 104 allowing to visualize the value of the parameters set in the microprocessor.

We claim:

1. An external device for injecting a medicament such as insulin into a human body comprising:
a casing for receiving a syringe to be fixed therein, said syringe comprising a housing containing the medicament and provided with an outlet part connected to a catheter for linking said housing to a human body, said syringe further comprising an internal plunger adapted for motion along said housing,
means held by said casing and energized by a spiral spring for actuating forwardly said internal plunger of said syringe;
a clockwork movement held by said casing regulated by a step electrical motor for regulating the motion of said internal plunger, and
means held by the casing for producing movement of said internal plunger additional to the electric motor regulated motion for instantaneous injection of doses of medicament.

2. An external device for injecting a medicament such as insulin into a human body comprising:
a casing for receiving a syringe to be fixed therein, said syringe comprising a housing containing the medicament and provided with an outlet part connected to a catheter for linking said housing to a human body, said syringe further comprising an internal plunger adapted for motion along said housing,
a main ratchet wheel rotatably mounted about an axis to said casing, a spiral spring having a first end and a second end, wherein said first end is attached to said main ratchet wheel and said second end is attached to said casing, a handle for stretching said spiral spring from outside said casing, gears transmitting the energy of said spiral spring to a sheath which is externally grooved for producing rotation of said sheath, said sheath being connected to the casing via a nut and a tube so that rotation of said sheath causes translation of said sheath and actuates forwardly said internal plunger of said syringe,
a clockwork movement held by said casing and regulated by a step by step electrical motor for regulating the motion of the internal plunger, and means held by the casing for actuating forwardly said internal plunger of the syringe additional to said electrical motor regulated motion.

3. An external device for injecting a medicament according to claim 2, wherein said clockwork movement comprises a gear engaged with said main ratchet wheel in order to regulate the speed of said main ratchet wheel.

4. An external device for injecting a medicament according to claim 3 further comprising a microprocessor for monitoring the speed of said step by step electrical motor.

5. An external device for injecting a medicament such as insulin into a human body comprising:
- a casing for receiving a syringe to be fixed therein, said syringe comprising a housing containing the medicament and provided with an outlet part connected to a catheter for linking the housing to a human body, said syringe further comprising an internal plunger adapted for motion along the housing,
- a main ratchet wheel rotatably mounted about an axis to said casing, a spiral spring having a first end and a second end, wherein said first end is attached to said main ratchet wheel and said second end is attached to said casing, a handle for stretching said spiral spring from outside said casing, gears transmitting the energy of said spiral spring to a sheath which is externally grooved for producing rotation of said sheath, said sheath being connected to said casing via a nut and a tube so that rotation of said sheath causes translation of said sheath and actuates forwardly said internal plunger of said syringe,
- a clockwork movement held by said casing and regulated by a step by step electrical motor for regulating the motion of said internal plunger, and
- a handle located outside said casing and connected to said sheath via a second ratchet wheel so that rotation of said handle in a first direction produces rotation of said sheath and permits the injection of an instantaneous dose of medicament and rotation of said handle in a second direction will not rotate said sheath.

6. An external device of injecting a medicament according to claim 5 wherein the casing further comprises an opening for permitting the position of said internal plunger of said syringe to be seen from outside said casing.

* * * * *